United States Patent
Doyle et al.

(10) Patent No.: US 10,072,231 B2
(45) Date of Patent: Sep. 11, 2018

(54) PROCESS FOR THE CONVERSION OF FREE FATTY ACIDS TO GLYCEROL ESTERS AND PRODUCTION OF NOVEL CATALYST SYSTEMS

(71) Applicants: Michael Phillip Doyle, Carmel, CA (US); Glenn Richards, Bakersfield, CA (US)

(72) Inventors: Michael Phillip Doyle, Carmel, CA (US); Glenn Richards, Bakersfield, CA (US)

(73) Assignee: AG Chem, LLC, Temecula, CA (US)

( * ) Notice: Subject to any disclaimer, the term of this patent is extended or adjusted under 35 U.S.C. 154(b) by 0 days.

(21) Appl. No.: 15/829,776

(22) Filed: Dec. 1, 2017

(65) Prior Publication Data

US 2018/0154325 A1    Jun. 7, 2018

Related U.S. Application Data

(60) Provisional application No. 62/429,585, filed on Dec. 2, 2016.

(51) Int. Cl.
*C11B 3/02* (2006.01)
*B01J 8/02* (2006.01)
(Continued)

(52) U.S. Cl.
CPC ............ *C11B 3/02* (2013.01); *B01D 17/0217* (2013.01); *B01J 8/0285* (2013.01);
(Continued)

(58) Field of Classification Search
CPC .... C11B 3/02; C11B 3/10; C07C 67/03; B01J 23/72; B01J 23/80; B01J 21/08; B01J 8/0285; B01J 29/65
See application file for complete search history.

(56) References Cited

U.S. PATENT DOCUMENTS 2,383,596 A    8/1945   Dreger
2,383,601 A    8/1945   Keim
(Continued)

FOREIGN PATENT DOCUMENTS

JP    S 59-32949    *  2/1988  .............. B01J 23/80

OTHER PUBLICATIONS

JPS 59-32949, Oosugi Minoru et al., Catalyst for synthesis of methanol, English Translation, 9 pages (Year: 1988).*

(Continued)

*Primary Examiner* — Yate Kai Rene Cutliff
(74) *Attorney, Agent, or Firm* — Christopher Darrow; Darrow Law Office

(57) ABSTRACT

Animal and seed based triglycerides are oils used in cosmetics, pharmaceuticals, animal feed, energy generation, etc. These triglycerides or glycerol esters are a mixture of triglycerides and free fatty esters (FFA) along with unsaponifiables and gums (MIU). FFA may range from very low, 1% or less, to more than 40% in some rendered animal oils. Corn oil from the wet or dry process of ethanol production may have from 7 to 15% FFA. The varying amount of FFA presents numerous process issues for downstream users of these oils especially in the production of biodiesel, fatty acid methyl ester (FAME). FFA about 1 or 2% requires esterification as well as transesterification for the production of FAME. What is needed is a method to perform Glycerolysis. This disclosure describes an improved catalyst system as well as process equipment and operating conditions to allow economical commercialization of Glycerolysis.

7 Claims, 1 Drawing Sheet

(51) Int. Cl.

| | |
|---|---|
| *C11B 13/02* | (2006.01) |
| *B01J 19/00* | (2006.01) |
| *B01J 21/08* | (2006.01) |
| *B01J 23/72* | (2006.01) |
| *B01J 37/04* | (2006.01) |
| *B01J 37/08* | (2006.01) |
| *B01D 17/02* | (2006.01) |
| *B01J 23/80* | (2006.01) |
| *C11B 3/10* | (2006.01) |
| *C07C 67/03* | (2006.01) |

(52) U.S. Cl.
 CPC ........... *B01J 19/0013* (2013.01); *B01J 21/08* (2013.01); *B01J 23/72* (2013.01); *B01J 23/80* (2013.01); *B01J 37/04* (2013.01); *B01J 37/08* (2013.01); *C07C 67/03* (2013.01); *C11B 3/10* (2013.01); *C11B 13/02* (2013.01); *B01J 2219/00051* (2013.01); *B01J 2231/49* (2013.01)

(56) References Cited

U.S. PATENT DOCUMENTS

| | | | |
|---|---|---|---|
| 2,494,366 A | 1/1950 | Sprules et al. | |
| 2,808,421 A | 10/1957 | Brokaw et al. | |
| 2,875,221 A | 2/1959 | Birnbaum | |
| 3,102,129 A | 8/1963 | Birnbaum et al. | |
| 3,459,736 A | 8/1969 | Dalibor | |
| 3,637,528 A * | 1/1972 | Stiles | B01J 23/80 502/236 |
| 4,164,506 A | 8/1979 | Kawahara et al. | |
| 4,267,393 A | 5/1981 | Torck et al. | |
| 4,303,590 A | 12/1981 | Tanaka et al. | |
| 4,698,186 A | 10/1987 | Jeromin et al. | |
| 4,956,286 A | 9/1990 | Macrae | |
| 5,399,731 A | 3/1995 | Wimmer | |
| 5,697,986 A | 12/1997 | Haas | |
| 5,713,965 A | 2/1998 | Foglia et al. | |
| 5,908,946 A | 6/1999 | Stern et al. | |
| 6,261,812 B1 | 7/2001 | Yamada et al. | |
| 6,399,800 B1 | 6/2002 | Haas et al. | |
| 6,423,857 B1 | 7/2002 | Copeland et al. | |
| 6,500,974 B2 | 12/2002 | Thengumpillil et al. | |
| 6,822,105 B1 | 11/2004 | Luxem et al. | |
| 7,619,104 B2 | 11/2009 | Clements | |
| 7,806,945 B2 | 10/2010 | Jackam et al. | |
| 7,871,448 B2 | 1/2011 | Jackam et al. | |
| 8,088,183 B2 | 1/2012 | Jackam et al. | |
| 9,365,801 B2 | 6/2016 | Agarwal et al. | |
| 2003/0083514 A1 | 5/2003 | Boocock | |
| 2007/0167642 A1* | 7/2007 | Oku | B01J 23/20 554/174 |
| 2008/0051592 A1* | 2/2008 | McNeff | C11C 3/003 554/170 |
| 2010/0286420 A1* | 11/2010 | Akatsuka | C07C 69/24 554/163 |
| 2011/0054200 A1 | 3/2011 | Cai et al. | |
| 2012/0048777 A1* | 3/2012 | Derr | B01J 21/12 208/120.01 |
| 2012/0123140 A1 | 5/2012 | Jackam et al. | |
| 2013/0012734 A1 | 1/2013 | Fukuhara et al. | |

OTHER PUBLICATIONS

Azhair, M. et al., Reduction of free fatty acids in crude Jatropha Curcas oil, via an esterification process, 2008, International Journal of Engineering and Technology, vol. 5, No. 2, pp. 92-98.

Felizardo, P., et al., Study on the glycerolysis reaction of high free fatty acid oils for use as biodiesel feedstock, 2011, Fuel Processing Technology, No. 92, pp. 1225-1229.

Davis Clements, "Pretreatment of High Free Fatty Acid Feedstocks", "Biodiesel Production Technology Workshop III", Mar. 26, 2003, pp. 78c-78i.

Felizardo et al, "Study on the Glycerolysis Reaction of High Free Fatty Acid Oils for Use as Biodiesel Feedstock", "Fuel Processing Technology", Jun. 1, 2011, pp. 1225-1229, vol. 92, No. 6.

Gerpen et al, "Biodiesel Production Technology", "National Renewable Energy Laboratory", Jul. 1, 2004.

\* cited by examiner

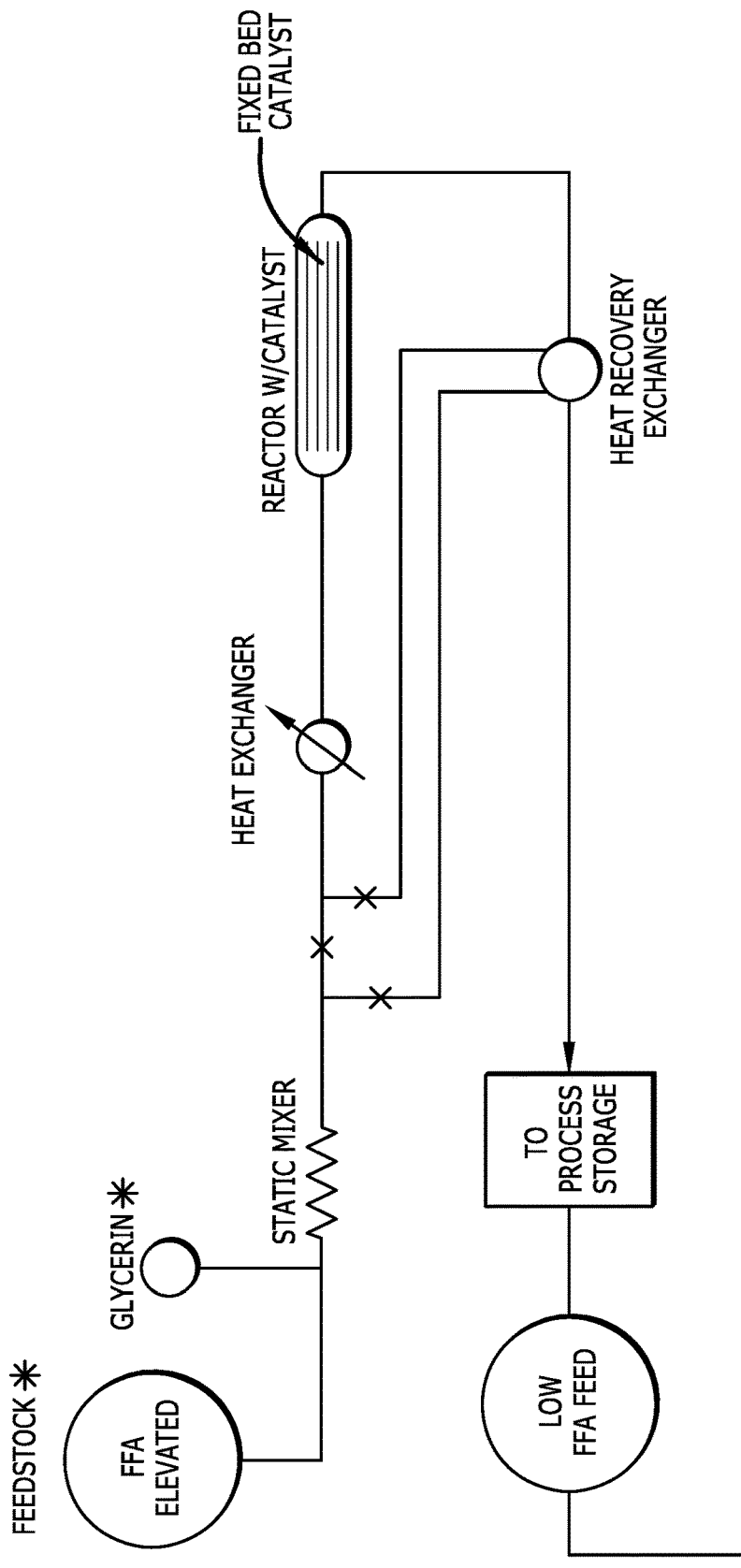

PROCESS FOR THE CONVERSION OF FREE FATTY ACIDS TO GLYCEROL ESTERS AND PRODUCTION OF NOVEL CATALYST SYSTEMS

RELATED APPLICATIONS

This application claims the benefit of and priority to U.S. Provisional Application Ser. No. 62/429,585, filed Dec. 2, 2016, the contents of which are incorporated by reference herein in its entirety.

FIELD OF THE DISCLOSURE

The present invention relates to an improved method of Glycerolysis seed and animal oils containing FFA. The method employees an improved catalyst and novel process equipment that results in an economical and fast method of Glycerolysis.

BRIEF DESCRIPTION OF DRAWINGS

The features of the invention will be better understood by reference to the accompanying drawings which illustrate the presently preferred embodiments of the invention. In the drawings:

FIG. 1 is a basic schematic of the process.

BACKGROUND OF THE INVENTION AND RELATED ART

Biodiesel, defined as fatty-acid alkyl ester (FAAE), or fatty acid methyl ester (FAME) is most commonly produced by a process of trans-esterification of triglycerides. The process involves reacting oils and fats with alcohol, usually methyl alcohol, in the presence of an alkaline catalyst. The conversion of triglycerides with alkaline catalysis is described in U.S. Pat. Nos. 2,383,601 and 2,494,366. The process is most efficient when the feedstock is a pure glyceride (refined oils and fats). The problem is that the price of the glycerides has increased dramatically over the last several years rendering it impossible to produce biodiesel that can compete with petrodiesel. Unfortunately, while cheaper feedstocks are available, they contain impurities including free fatty acids (FFA) that require additional processing, such as esterification or other, thus increasing the cost of producing biodiesel. The challenge is to develop processes that can allow production of cheaper feedstocks for producing biodiesel in one step.

The literature includes a number of approaches of dealing with FFA (see, Brown Grease Feedstocks for Biodiesel (2002) WWW domain nrel.gov, 2002, pp. 1-33, National Renewable Energy Laboratory, Boulder, Colo.). One of the options is to strip the FFAs from the oil. This is a well-known process, also known as physical refining or steam distillation. In this process, the FFA is stripped (evaporated) from the oil under vacuum. The FFA is condensed and recovered. The advantage of this process is that it produces oil that is practically free of FFAs and a very good feedstock for producing biodiesel. A challenge with this process is that there is a reduction in the amount of oil available to produce biodiesel due to loss of FFA and some neutral oil during the stripping process. Consequently, the higher the FFA the higher the yield loss and the lower the attractiveness of this approach. An example of this process of recovering fatty acids is set out in U.S. Pat. No. 6,423,857. This patent focuses on pre-treating high phospholipid containing oil (such as soybean oil) prior to steam distillation and subjecting the oil to steam distillation that produces a distillate containing at least about 97 percent by weight free fatty acids.

Another option is to react the FFAs with an alcohol, usually methyl alcohol, in the presence of an acid catalyst to produce FAAE/FAME. For instance, U.S. Pat. No. 4,164,506 discloses a biodiesel synthesis wherein fatty acids are subjected to acid catalysis. This process is called acid esterification and would be very attractive if it could convert all FFA into FAAEs. Unfortunately, this process poses several challenges: (a) un-reacted or unconverted FFA left in the oil after esterification must be removed with additional intermediate steps and equipment; (b) the esterification process requires use of acidic catalyst which poses risk to people (risk of burning skin and flesh upon contact) as well as equipment (risk of corrosion upon contact); and (c) the esterification process requires a large quantity of excess methanol (needed to maintain the proper equilibrium for advancing the reaction which is inhibited by the formation of water during esterification) thus increasing the emission of volatile substance in the atmosphere. The acid esterification is especially unattractive when the FFA content is higher because a large amount of acid catalyst and methyl alcohol are required in order to convert feedstocks having high FFA content. Water of reaction is also poses additional downstream processing problems as well as inhibiting esterification. Since the acid catalyst must be neutralized with alkali before processing the glycerides, the increased catalyst loading results in an excessive amount of salts produced as a consequence of alkali neutralization. Further, such processes generate a large volume of waste water as revealed in the disclosures of U.S. Pat. Nos. 4,303,590, 5,399,731 and 6,399,800.

Alternatively, solid catalysts can be used for the acid esterification reaction to avoid a neutralization step before the transesterification reaction. These processes have been extensively explored and documented, such as in U.S. Pat. No. 3,459,736 (which uses titanium oxide as a catalyst), U.S. Pat. No. 4,698,186 (which utilizes various solid catalysts), U.S. Pat. No. 4,267,393 which uses sulfonated resins as solid acid catalysts and U.S. Pat. No. 5,908,946 which employs zinc and aluminum oxide as catalysts for the esterification reaction).

U.S. Pat. Appl. No. 2003/0083514 discloses a single-phase process for production of fatty acid methyl esters from mixtures of triglycerides and fatty acids. This process is limited in that it requires acid catalyzed esterification of fatty acids prior to the transesterification step. U.S. Pat. No. 2,383,596 discloses a method for esterifying fatty acid and trans-esterifying glycerides. This process is limited in that only an esterification step is disclosed.

A third option is enzymatic catalysis. The conversion of both free fatty acids and triglycerides with enzyme catalysis is disclosed in U.S. Pat. Nos. 4,956,286, 5,697,986 and 5,713,965. A representative example of the esterification or transesterification method is disclosed in JP-B 6-65311, in which fatty acids or lower alcohol esters thereof are reacted with glycerol in the presence of an immobilized lipase having 1,3-position selectivity and the byproduct water or lower alcohol formed by the reaction is removed from the system at a reduced pressure to obtain the diglycerides. This reaction is preferably conducted in the presence of an enzyme having an ester activity, such as a lipase or an esterase, preferably in the presence of an immobilized or intracellular lipase having 1,3-position selectivity. Known methods for immobilization are described, for example, in "Koteika Koso (Immobilized Enzyme)," edited by Ichiro Chihata, published by Kodansha Ltd. Publishers, pp. 9-85 and "Koteika Seitai-shokubai (Immobilized Biocatalyst)" edited by Ichiro Chihata, published by Kodansha Ltd. Publishers, pp 12-101. Immobilization onto an ion-exchange resin is preferred. Lipases having 1,3-position selectivity and usable in immobilization include those derived from microorganisms of, for example, the genera *Rhizopus, Aspergillus, Mucor*, etc., as well as pancreatic lipases, and the like. For example, use can be made of the lipases derived from *Rhizopus delemar, Rhizopus japonicus, Rhizopus niveus, Aspergillus niger, Mucor javanicus*, and *Mucor miehei*. A commercial immobilized lipase having 1,3-position selectivity is Lipozyme® IM, manufactured by Novo-Nordisk Bioindustry A.S. An intracellular lipase having 1,3-position selectivity comprises a lipase having 1,3-position selectivity adsorbed or bonded to microbial cells. A commercially available example thereof is Olipase™, manufactured by Nagase & Co., Ltd. This process is challenging because the reaction produces water which inhibits the forward reaction. Other problems with enzymatic processing are the slow reaction rates and high cost of enzymatic catalysts. Further, enzymatic catalysts have a limited life. These shortcomings when compared to alkaline and acidic reactions render the enzymatic processes economically unfavorable.

A fourth option is described in US Pat. Appl. No. 2012/0123140 involving glycerolysis of high free fatty acid (HFFA) oil. This process converts FFAs into oils through esterification of fatty acids with glycerol. The resulting product is oils which are fatty acid glycerin esters (or FAGE). This process is variously known as glycerolysis, alcoholysis, or esterification. Glycerolysis of fats and oils with glycerol has been intensively researched during the 1940's and 1950's. Sonntag (1982) (Sonntag, N. o. V., glycerolysis of Fats and Methyl Esters—Status, Review, and Critique, Journal of American Oil Chemists Society 59:795A-802A) has a complete collection of these patents in his review. The reaction produces a mixture of mono-, di- and tri-glycerides.

For example, U.S. Pat. No. 3,102,129 discloses a process for producing monoglycerides of fatty acids and U.S. Pat. No. 2,875,221 discloses a process for preparing monoglycerides of fatty acids. These processes are limited in that they require admixing a substantial proportion of previously reacted monoglyceride product with a freshly mixed stream of glycerol and fat and rapidly heating the mixture on a hot surface. U.S. Pat. No. 6,500,974 discloses a process for preparation of a monoglyceride. This process is limited in that the presence of a food grade polar solvent is required in the glycerolysis reactor.

Although the esterification or transesterification method is a process in which fatty acids or lower alcohol esters thereof and glycerol are converted to partial diglycerides through a one-step reaction, it is not cost efficient because the individual feedstock materials are expensive. For conducting the second stage esterification reaction, glycerol is added to the partial decomposition product, obtained through the first-stage reaction in such an amount that the mole number of fatty acid groups in the decomposition product mixture of the first stage is from 0.8 to 2.5 mol per 1 mol of glycerol groups based on the total of glycerol groups of the decomposition product mixture of the first stage and glycerol groups added to the second stage (see, e.g., U.S. Pat. No. 6,261,812).

On the other hand, U.S. Pat. No. 2,808,421 discloses a method for preparing mixed triglyceride compositions using a titanium alcoholate catalyst. U.S. Pat. Nos. 7,806,945, 8,088,183, 7,871,448, and US. Pat. Appl. No. 2012/0123140, disclose a process for preparation of fatty acid methyl ester using HFFA oil. The process includes glycerolysis as part of their overall process. The conditions taught for glycerolysis of free fatty acids (at a temperature of about 220.degree. C and at a pressure of about 2 pounds per square inch absolute) in a glycerolysis reaction without a catalyst to produce a glycerolysis reactor effluent stream that contains less than 0.5 percent by weight of free fatty acids and a plurality of glycerides, are similar to other literature. These patents teach there is a need for at least two continuous stirred tank reactors that are operated in series with a combined residence time of not more than about 500 minutes. For a 20% FFA stream, the time taken is no more than 200 minutes. A problem with this approach is that, despite claims to the contrary, it only efficiently reduces the FFA by 80-90%, thus making it necessary to either use catalysts or add intermediate steps and equipment to reduce the remaining FFA either chemically or physically. Moreover, the size of glycerolysis reactors is large because it is sized to handle the entire mass of oil even though the FFA content is a relatively small portion of that stream and consequently there is a waste of energy because a greater amount of material (the entire HFFA oil stream) is subject to higher temperature and then cooled down when it is only necessary to heat the FFA.

The background art is also characterized by a number of non-patent publications. Noureddini et al. in glycerolysis of Fats and Methyl Esters, JAOCS, 1997, pp. 419-425, vol. 74, no. 4 discloses the glycerolysis of methyl esters and triglycerides with crude glycerin. The main focus of their study is on utilization of "crude" glycerol obtained from the bio-diesel industry as opposed to "pure" glycerin previously used in glycerolysis to mono-, di-, and tri-glycerides. They did not disclose glycerolysis of fatty acids and their focus was on production of mono- and di-glycerides from FAME and tri-glycerides using crude glycerin.

Felizardo, et al. in "Study on the glycerolysis reaction of High Free Fatty Acid Oils for Use as Biodiesel Feedstock", Fuel Processing Technology, 2011, pp 1225-1229, vol. 92, no. 6, discloses the conversion of oils with a high content of FFA (20-50%) by esterification with glycerol. The results suggest that the FFA content could be reduced from 50% to 5% in 3 hours at 200 degree. C. without the use of a catalyst. The presence of a zinc-based catalyst reduced the reaction time to 1 hour and reduced the FFA to 1.2%.

Canakci, M. and J. Van Gerpen (2001) in Biodiesel Production from Oils and Fats with High Free Fatty Acids, Transactions of the American Society of Agricultural Engineers, 44(6):1429-1436 discloses that "glycerolysis" is an alternative process that can be used with feedstocks containing more than 10% FFAs. This involves adding glycerin at 400.degree. F. and letting it react with the FFAs to form monoglycerides, a glycerol molecule to which one free fatty acid has been joined. These monoglycerides can then be processed using a standard alkaline catalyst transesterification process. Waste glycerin from biodiesel processing can be used in this process. Glycerolysis can be expensive because of the high heat involved, which requires a high-pressure boiler and trained boiler operator. Also, a vacuum must be applied while heating to remove water that is formed during the reaction. Another disadvantage is that the glycerin will also react with the triglycerides in the oil to convert some of them to monoglycerides. While this does not negatively impact the reaction, it means that more glycerin is required for the process, and therefore more glycerin must be removed at the end of the transesterification.

Kumoro in "Experimental and Modeling Studies of the Reaction Kinetics of Alkaline-Catalyzed Used Frying Oil Glycerolysis using Isopropyl Alcohol as a Reaction Solvent, Research Journal of Applied Sciences, Engineering and Technology 4(8): 869-876, 2012, discloses a glycerolysis process using isopropyl alcohol and an alkaline catalyst. However, the focus of this and several other researches is to convert tri-glycerides to mono-glycerides for use in foods, cosmetics, and pharmaceutical products. This study is not directly relevant to our invention because it does not address glycerolysis of fatty acids.

Tyson in Brown Grease Feedstocks for Biodiesel, WWW domain nrel.gov, 2002, pp. 1-33, National Renewable Energy Laboratory, Boulder, Colo., discloses techniques for converting greases to biodiesel. The techniques disclosed in this reference are limited. Moreover, the conditions taught for glycerolysis of free fatty acids are at temperatures in the range of 250.degree. C. to 260.degree. C. in the absence of a catalyst or at 220.degree. C. with a catalyst. The reference teaches that there is "no proven technology for 50+% FFA mixes" and that "combined processes for ASTM [American Standard for Testing and Materials] quality biodiesel not well developed, technical and economic questions exist."

Tyson in Biodiesel Technology and Feedstocks, WWW domain nrel.gov, 2003, pp. 1-37, National Renewable Energy Laboratory, Boulder, Colo., includes much of the same information as contained in her 2002 presentation. The reference notes that using "glycerolysis to treat FFA" to "convert FFA to monoglycerides, then transesterify" is "commercial, not currently used in biodiesel."

Davis Clements in Pretreatment of High Free Fatty Acid Feedstocks, Biodiesel Production Technology Workshop III, Mar. 26-28, 2003, pp. 78c-78i, University of Nebraska, Lincoln, Nebr., discloses a number of methods for pretreatment of high free fatty acid feedstocks prior to transesterification. This process is limited in that glycerolysis is carried out at 200.degree.C. under an 11 pounds per square inch vacuum, usually with a catalyst such as zinc chloride, with venting of water. This process is further limited in that, in the absence of a catalyst, a residence time of over 5 hours is required to achieve an effluent containing less than 1 percent free fatty acids.

SUMMARY OF THE DISCLOSURE

We have listed the prior art and their merits and problems. Moreover, the goals of many prior art works pertaining to glycerolysis have been different. One stream of research has addressed the conversion of tri-glycerides to mono-glycerides for the purpose of producing emulsifiers used in foods, cosmetics, and pharmaceutical products. On the other hand, the goal of converting fatty acids to glycerides is more relevant to the present invention. However, the attempt of the prior art has been to obtain close to full conversion of fatty-acids to glycerides. The goal of the present invention is to not only obtain full conversion but to do so economically, with an advanced catalyst in a reaction process under specific operating condition that make the conversion in less time and at a lower temperature saving energy. This novel process follows some basic process steps. First step, combine the feedstock and the glycerin (crude neutralized or tech grade) in a specific ratio based on the FFA of the feedstock. Second step, raise temperature to between 380 and 400 F, removing all water during this step. Third step, pump the heated mixture into a reaction vessel which contains a specific fixed bed catalyst. Fourth step, provide the minimum reaction time for complete conversion. Fifth, during the reaction period, the process must remove water of reaction to allow for a complete reaction in a short period of time.

Description of Catalyst
General Criteria

There are two basic types of catalysts that can be used for these processes. They are a homogeneous catalyst and a heterogeneous catalyst. The basic difference is that in a homogenous catalyst, the catalyst and reactants are in the same phase, specifically a liquid, solid or vapor. One example might of a homogeneous catalyst might be the use of sulfuric acid in a liquid phase with the methanol, free fatty acids and glycerol esters (esterification example). Note that the use of oils and water based liquids often leads to separation of liquids which can be exploited using gravity separation.

The disadvantages of homogeneous catalysts in biodiesel synthesis is that they usually form soaps and require washing. Some catalysts are water soluble salts such as zinc acetate which do well in terms of allowing for lower reaction temperatures but present serious problems for the cleanup of reactants.

Some catalysts cross boundaries of solids and liquid phases. One example might be the use of zinc metal as solids or powders which are slowly consumed during the reaction sequence. The reactions in biodiesel synthesis using zinc as elemental zinc are problematic given they generate soluble forms of zinc as well as zinc granules and particulates as the breakdown products of solid zinc wire, rods or plate materials.

Other catalysts cross boundaries which can react both in the vapor space and liquid phases as well. These often have a range of temperatures and pressures which cause the FFAs and FAMEs to be in the liquid and gas phases in reactors that use solid catalysts of varying particle size ranges.

The general or overall goals of catalysts from biodiesel synthesis are to lower the reaction temperatures, reduce formation of tars and high molecular weight gums common in oil synthesis reactions. In the case of FFA conversion, the downward shift in reaction temperatures may be as little as a few degrees and up to 50 F. In the case of cat cracking the temperature reduction may be over 100 F. Alternatively, the reaction temperatures may be the same but allow the reaction time to be reduced, by anywhere from 5% to 50% for equipment reaction byproducts.

Other means to reduce reaction temperatures with a catalyst of the same chemical composition is to synthesize catalysts with higher surface area and greater pore volumes to accelerate the reaction and drive it in the forward direction.

Other catalysts are focused on oxygen scavenging. The key in design and selection of catalysts for this function is which byproducts are going to be formed. In the case of supported oxide catalysts, the reaction for oxygen reduction or elimination can generate $CO_2$, CO or $H_2O$ as a means to convert free or dissolved oxygen into a gas that will escape in the reaction exhaust. In the case of CO, to meet and comply with EPA regulations, it is necessary to use a thermal oxidizer on the outlet gases to convert the CO to the fully oxidized $CO_2$. The more that the reaction byproducts are shifted towards $CO_2$ versus CO, the lower the temperature of the oxidation reaction and the lower the consumption of fuel to fully oxidize vapors usually done at 1400 F.

The catalysts used may be synthesized in several ways. In the case of metal powders, sintering and compression can be used to form most common shapes including cylinders, spheres and rods. Heat and pressure are uses in combination to hold the material together. Other more unique methods include mixing of powders such as oxides or elemental metals with PAC (Powered Activated Charcoal) followed by addition of a binder, compression and the application of heat. The advantage of these catalysts is an ability to design more even temperature profiles and avoid hot spots in the reactor beds, also called exotherm moderation.

Other catalyst methods include "doping" of the catalyst granules to partially deactivate the reaction. This is usually for an adiabatic reactor that is insulated that may otherwise "runaway" in terms of reaction temperature. It is possible in biodiesel synthesis catalysts to emulate or simulate an isothermal reactor by judicious use of catalyst deactivation creating a graded bed wherein the most reactive portion is on the top and the least reactive portion in on the bottom of the reactor. This can be done for reaction tubes or for an open cylindrical bed. Furthermore, in cracking or higher temperature reactions, the bed can be designed to have a gradient both by height and via radius.

Another factor in catalyst design is whether or not the reactant vapors or liquids are allowed to recycle back into the reactor. The purpose in general of vapor recycle loops is to operate at lower reaction temperatures to limit any unfavorable byproducts or to achieve higher reaction conversion rates, at the sacrifice of lower overall throughput of reactants.

Finally, two or more catalysts may be formed into a single solid or liquid phase as a single catalyst or a blend of two or more on substrates such as silica or alumina.

Cracking Catalyst

There are number of cracking catalysts that have been used in the past. In general, most fall in the category of single phase silica or alumina, meaning one metal oxide supported at a time. Each metal oxide forms a different reaction product mix. As a liquid or vapor passes through the reaction zone, and as the reaction byproduct blend or composition changes, there I an optimal blend of catalysts which is also a function of reaction temperature.

It is also now possible to synthesize a heterogeneous catalyst with multiple metal oxides on the same or even a mixed support. For example, copper oxide (CuO) on alumina may be a common catalyst to use for cracking. Copper oxide can also be blended with zinc oxide (ZnO) as powders using any desired weight ratio. A blend of three oxides can also be made such as a blend of CuO, ZnO and manganese oxide (MnO2).

In one aspect of this disclosure, a heterogeneous calcined catalyst is provided with the preferred combination comprising approximately 90% colloidal silica, approximately 18% zinc oxide powder and approximately 2.3% copper oxide. Depending on the combinations chosen, these values can have ranges of 1% to 95% silica, 0.0% to 5% copper oxide and 1% to 25% zinc oxide.

For cat cracking the reactor bed can also be graded or have layers of different metal oxides. Although some expensive metals such as palladium on alumina have been used in the past, for biodiesel, given the low sales price of the end-product, it is vital to design a catalyst to be low in cost and survive for an extended period of time to amortize the cost of the catalysts.

Some cat cracking catalysts of interest include ZSM-5 which has been used in the prior art to shift the reaction byproducts more towards the gasoline fraction versus the diesel fraction. These types of silica-aluminate ordered catalysts can be used by blending into the catalyst bed or it can involve the use of layers in the bed.

A list of possible catalysts for FFA conversion includes the following as individual catalysts, mixed beds or layered beds or even layered tubes. Tube diameters of three inches or less are common to achieve semi-isothermal gradients vertically.

| | | |
|---|---|---|
| CuO/Alumina | CuO/Silica | ZSM-5 |
| CuO/ZnO/Silica | MnO2/Silica | MnO2/ZnO/Silica |
| ZnO/Alumina | ZnO/Silica/Alumina | CuO/ZnO/MnO2/Silica |
| ZnO/Silica | Alumina | CuO/MnO2/Silica |

Note that alumina catalysts are often fabricated as spheres so they have low pressure drop in vapor phase reactors. It is common to use the large spheres on the bottom of the bed and progressively use small spheres or balls.

Additional features of the process include the following. Using the disclosed compositions, a catalyst may be formed into a 3D shape including annual cylinders with hollow centers or cores (aka Cheerios) calcined at 350 C to 600 C. Hollow static mixers may also be formed allowing the oil to flow through under pressure both inside and outside the formed shape ranging in size from 6" to 30" in length. An internal or external guard bed may be utilized for the oil flowing over the catalyst to act as a low pressure drop particulate filter at temperatures ranging from 150 C to 250 C and made from the silica or alumina.

Additionally, the catalyst may be used at the disclosed temperature ranges and compositions to shift the oil composition of mono, di and triglycerides preferentially to a product composition higher in triglycerides, aka a "glyceride shifter". Further, nano ceramic filters may be used to reduce nitrogen via particulate removal from the oil ranging in size from 1 micro down to 40 nm (nanometers) preferentially while the oil is in the temperature range of 70 C to 90 C.

Applying electrocoagulation to the oil prior to exposure to the catalyst will increase pellet longevity by reducing the presence of particulates and compounds that might otherwise plug the catalyst pores. Ultrasonic transducers may be placed in the flow path of the oil to accelerate the reaction rates and to permit lower temperatures of operation without generation of darkened oil in a temperature range as low as 70 C and ranging up to 200 C depending on the maximum temperature rating on the transducer.

The disclosed catalysts may be used other than for glycerolysis such as oxidation, reduction of carbon monoxide and redox of both liquid and vapor. Also, the reactor may be configured to provide for the catalyst to be supported in the vapor phase with or without a guard bed to accelerate the reaction rates.

Example 1: ZnO/Silica Catalyst

ZnO powder with a particle size of 80 nm is added to HS40 colloidal silica made by WR Grace. A total of 20 grams of powder are blended into the 40% by weight colloidal silica. Then 50 cc of ammonium hydroxide 15% by weight is added to the blend of ZnO powder and Ludox and stirred to get a uniform paste. That paste is then oven dried at 120 C for 12 hours. The resulting cake is crushed and using a sieve shake made into particle sizes in the 4 to 60 mesh size. The dried material is then calcined at approximately 400 C for 8 hours. A preferred range is 350 C to 550

C. The temperature can be higher, but this will result in a reduced surface area and reaction rate.

Example 2: ZnO/CuO/Silica Catalyst

Same as example 1 except add in 10 grams of zinc oxide powder and 10 grams of copper oxide powder.

Example 3: ZnO/CuO/MnO2/Silica Catalyst

Same as example 1 except add in 6.67 gm zinc oxide powder, 6.67 gms of copper oxide powder and 6.67 gms of manganese oxide powder.
Zinc Catalysts A common catalyst is zinc, in various forms including zinc metal, zinc wire as elemental form, zinc acetate, zinc chloride and various zinc oxides partially dissolved in HCl, phosphoric or sulfuric acids. These last in the reactor for a few days. As wire diameter increases, longevity increases but the metal waste from cracked wires and fragile pieces, also increases with larger diameter wires. Zinc may also be used by forming anodes and cathodes similar to those used for electro-coagulation. These typically last for one or two weeks.

In general, it is not economical to pursue zinc as elemental or zero charge for a catalyst for biodiesel production. There are several new methods developed to take greater advantage of the zinc powder or zinc dust, including sintered powders or extruded porous zinc or compression of zinc powder with activated powder to form cylindrical shapes.

Zinc in the +2 valence state however, is a more interesting an economical choice as a catalyst but it requires supporting the zinc compound on a substrate such as silica or alumina. One example is the use of zinc oxide which is a common household ingredient for toothpaste and suntan blocker oils. The common substrates for the powdered zinc formed into larger particle size catalysts are silica and alumina. For silica, Ludox is commonly used which is colloidal and is easily blended with metal oxide powders. A paste can be formed by shifting the pH using ammonium hydroxide. The resulting metal oxide paste can be oven dried then calcined in air. The calcine oven exhaust needs to be scrubber using water or a slightly acidic spray such as citric acid.

Example 1: Zinc Metal Powder in Carbon Matrix 2,000 gms of zinc dust (zinc powder—100 mesh), is blended with 6,000 gms of PAC (Powdered Activated Charcoal). To the blend a binder is added which can survive curing at 350 C under compression. A cylindrical mold is used for a 20 inch longer 4.5 inch diameter standard filter cartridge. That can be used in stainless steel housings pumping the biodiesel through under pressures up to 100 psig. The maximum reaction temperature is limited by the carbon binder.

Example 2: Zinc Metal Powder Sintered 8,000 gms of zinc powder is added to a compression mold and put under pressure (100 psig) and heat (320 C). The mold is released after application of a mold release compound. The compressed porous cylinder is then heated to 550 C to fuse some of the powdered zinc or zinc dust. That piece can be used in the stainless steel housing and have oil pumped through it.

Example 3: Zinc Oxide Nanoparticles on Silica 2,000 gms of zinc oxide nanoparticle of <80 nm particle size, is mixed with Ludox for form a 10% by weight supported catalyst. The paste is dried in an oven at 130 C for 8 hours. The dried cake is then crushed and sized to take the 8 to 50 mesh fraction which is then calcined at 400 C to 4 hours. This solid material is put into stainless steel mesh sock filters and loaded into an insulated filter housing.

Examples of the Invention

The procedure for testing is as follows and was used on all example batches.
Step 1—test feedstock (note feedstock type) in question for water content and FFA %
Step 2—test the glycerin for pH and water content, note if crude (and % glycerin) or USP grade
Step 3—combine in a 500 ml beaker, 253.6 grams of feedstock with 45.6 grams of glycerin (of at least 90% glycerin content, increase amount if not 90%).
Step 4—on a stirring hotplate, heat feed and glycerin to 385 F, stir constantly.
Step 5—add 2 grams (or none as baseline) of the desired catalyst (note catalyst type).
Step 6—while stirring and maintain 385 F, react for 60 minutes, testing the FFA at 15 minute intervals. Leave beaker open to allow water vapor from reaction to escape.
Feedstocks to test; Corn oil, 1% moisture, 10.1% FFA
   UCO, 1.5% moisture, 6.25% FFA
   Beef Tallow, 1% moisture, 9% FFA
Glycerin; USP glycerin purchased locally
Crude animal based glycerin, 93% glycerin, 0.5% moisture. Balance 2% FAME, 4.5% other.

| Catalysts; | | |
|---|---|---|
| | SnCL2/SiO2 | 1 |
| | CuO/ZnO(1x)/SiO2 | 10 |
| | CuO/ZnO (2x)/SiO2 | 10(2) |
| | CuO/ZnO (3x)/SiO2 | 10(3) |
| | ZnO/SiO2 | 7 |
| | TiO2/SiO2 | 4 |
| | ZnO/AL2O3/SiO2 | 6 |
| | MnO2/TiO2/AL2/MgO/ZnO/SiO2 | 13 |

Examples

Using above procedures, test a series of colloidal based catalysts.

| Feedstock | Glycerin Type | Catalyst | Ending FFA | Time (min) |
|---|---|---|---|---|
| Corn Oil | USP | 10 | 0.4 | 45 |
| Corn Oil | USP | 6 | 0.95 | 45 |
| Corn Oil | USP | 1 | 2.39 | 45 |
| Corn Oil | USP | 7 | 0.74 | 45 |
| Corn Oil | USP | 4 | 1.18 | 45 |
| Corn Oil | USP | 13 | 0.74 | 45 |
| UCO | crude | 10(1x) | 1.03 | 45 |
| UCO | crude | 10(2x) | 0.64 | 30 |
| UCO | crude | 10(2x) reuse | 0.56 | 30 |
| UCO | crude | 10(3x) | 0.53 | 15 |
| Beef | crude | 10(3x) | 0.82 | 45 |

From the example data, observations can be made regarding reactivity of glycerin type, USP or crude. During our work, we found high purity crude glycerin to be very reactive, more than USP. We also repeated numerous batches using the same 2 grams of catalyst finding no loss of reaction. We constructed a lab unit, capable of processing 25 gallons of feedstock continuously and found reaction times decreased to minutes when passed over a packed bed catalyst system. After this small 25 gallon pilot unit trial, we conducted full scale, truck load quantities (>3500 gallons) using a jacketed tank with a center shaft mixer. A "kidney" style loop to a 400 gallon vessel packed with our preferred catalyst was installed. We conducted trials with and without the kidney loop to compare conversion times. Without the kidney loop, reaction of glycerin and triglyceride alone, no reaction was observed at 350 F. With the loop in operation, mixture passing through kidney loop and across the packed bed, reaction occurred at 350 F and in 90 minutes the FFA reduced from 29% to under 5%.

Excess glycerin is removed from the FFA reduced oil. Excess glycerin is 1% to 15% by weight defined as glycerin unreacted after heating with or without catalyst to convert to oil. The amount of excess can be higher but this will slow down reaction rate.

In another aspect, the mixture of the feedstock oil and crude glycerin may be combined in a heating vessel wherein the glycerin is approximately 1.2% times the amount of the weight of FFA in the feedstock oil. In yet another aspect, the FFA can be in the range of 0.1% to 75% by weight as compared to the glycerin.

Further Examples of the Disclosure

The processes discussed above can be additionally described as follows.

1. A method for reducing the free fatty acid (FFA) of a feedstock oil containing approximately 2% to 100% FFA, the method comprising
   providing a heterogeneous calcined catalyst comprising approximately 90% colloidal silica, approximately 18% zinc oxide powder and approximately 2.3% copper oxide;
   placing the catalyst in a fixed bead multiple reactor;
   in a heating vessel, combining a mixture of the feedstock oil and crude glycerin wherein the glycerin is approximately 1.2% times the amount of the weight of FFA in the feedstock oil;
   heating the combined mixture to approximately at least 385 F for driving off moisture, said moisture to become less than about 0.25% of the resultant mixture;
   pumping the resultant mixture across the catalyst bed in the fixed bead multiple reactor thereby producing an FFA reduced oil; and
   removing excess glycerin from the FFA reduced oil.

2. The method of item 1 above wherein the calcined catalyst is produced by a method comprising:
   by weight of total, combining approximately 90.0% of a colloidal silica, approximately 6.8% zinc oxide powder and approximately 2.3% copper oxide powder and mixing to form a slurry;
   placing the slurry in an oven and heating at a temperature of approximately 200 C until an essentially liquid free product is formed;
   removing the essentially liquid free product from the oven, sizing said product to approximately 5 to 35 mesh; and
   placing said product in an oven and calcining at approximately 400 C.

3. The method of item 1 above wherein the excess glycerin is removed from the FFA reduced oil in a centrifuge.

4. The method of item 1 above wherein the resultant mixture is pumped across the catalyst bed a second time as required for contact time for producing the FFA reduced oil.

5. A method for reducing the free fatty acid (FFA) of any FFA containing oil including an animal derived oil, seed derived oil, paper processing derived oil, tall oil or any other FFA containing oil to less than approximately 1% FFA from an oil that may contain from about 2% to 100% FFA, the method comprising the steps of:
   producing an engineered heterogeneous catalyst by the following steps; a) by weight of total, combining approximately 90.0% of a colloidal silica, approximately 6.8% zinc oxide powder and approximately 2.3% copper oxide powder and mixing to form a slurry; b) placing in oven and heating at a temperature of approximately 200 C until a liquid free product is formed; c) removing from oven, sizing product to approximately 5 to 35 mesh as required; d) placing product in oven and calcining at approximately 400 C;
   placing the catalyst in a fixed bead multiple reactor;
   in a heating vessel, combining a mixture of the feedstock oil and crude glycerin wherein the glycerin is approximately 1.2% times the amount of the weight of FFA in the feedstock oil;
   heating the combined mixture to approximately at least 385 F for driving off moisture, said moisture to become less than about 0.25% of the resultant mixture;
   pumping the resultant mixture across the catalyst bed in the fixed bead multiple reactor thereby producing an FFA reduced oil; and
   processing the FFA reduced oil through a centrifuge or other device to remove excess glycerin.

6. The method of item 5 above wherein the resultant mixture is pumped across the catalyst bed additional times as required for contact time for producing the FFA reduced oil.

7. A method for reducing the free fatty acid (FFA) of a feedstock oil containing approximately 2% to 100% FFA, the method comprising
   providing a heterogeneous calcined catalyst comprising approximately 1% to 95% colloidal silica, approximately 1% to 25% zinc oxide powder and approximately 0% to 5% copper oxide;
   placing the catalyst in a fixed bead multiple reactor;
   in a heating vessel, combining a mixture of the feedstock oil and crude glycerin wherein the glycerin is approximately 1.2% times the amount of the weight of FFA in the feedstock oil and wherein the FFA is approximately 0.1% to 75% by weight;
   heating the combined mixture to approximately at least 385 F for driving off moisture, said moisture to become less than about 0.25% of the resultant mixture;
   pumping the resultant mixture across the catalyst bed in the fixed bead multiple reactor thereby producing an FFA reduced oil; and
   removing excess glycerin from the FFA reduced oil.

Reasonable variation and modification are possible within the scope of the foregoing disclosure, the drawing and the appended claims of the invention, the essence of which is that there has been provided a method for treating high FFA renewable feedstock. Numerous variations and improvements are possible by those skilled in the art. Therefore, the claims define the invention, which is not limited to the disclosure above.

We claim:

1. A method for reducing the free fatty acid (FFA) of a feedstock oil containing approximately 2% to 100% FFA, the method comprising
   providing a heterogeneous calcined catalyst comprising approximately 90% colloidal silica, approximately 18% zinc oxide powder and approximately 2.3% copper oxide;
   placing the catalyst in a fixed bead multiple reactor;

in a heating vessel, combining a mixture of the feedstock oil and crude glycerin wherein the glycerin is approximately 1.2% times the amount of the weight of FFA in the feedstock oil;

heating the combined mixture to approximately at least 385 F for driving off moisture, said moisture to become less than about 0.25% of the resultant mixture;

pumping the resultant mixture across the catalyst bed in the fixed bead multiple reactor thereby producing an FFA reduced oil; and removing excess glycerin from the FFA reduced oil.

2. The method of claim 1 wherein the calcined catalyst is produced by a method comprising:

by weight of total, combining approximately 90.0% of a colloidal silica, approximately 6.8% zinc oxide powder and approximately 2.3% copper oxide powder and mixing to form a slurry;

placing the slurry in an oven and heating at a temperature of approximately 200 C until an essentially liquid free product is formed;

removing the essentially liquid free product from the oven, sizing said product to approximately 5 to 35 mesh; and placing said product in an oven and calcining at approximately 400 C.

3. The method of claim 1 wherein the excess glycerin is removed from the FFA reduced oil in a centrifuge.

4. The method of claim 1 wherein the resultant mixture is pumped across the catalyst bed a second time as required for contact time for producing the FFA reduced oil.

5. A method for reducing the free fatty acid (FFA) of any FFA containing oil including an animal derived oil, seed derived oil, paper processing derived oil, tall oil or any other FFA containing oil to less than approximately 1% FFA from an oil that may contain from about 2% to 100% FFA, the method comprising the steps of:

producing an engineered heterogeneous catalyst by the following steps; a) by weight of total, combining approximately 90.0% of a colloidal silica, approximately 6.8% zinc oxide powder and approximately 2.3% copper oxide powder and mixing to form a slurry; b) placing in oven and heating at a temperature of approximately 200 C until a liquid free product is formed; c) removing from oven, sizing product to approximately 5 to 35 mesh as required; d) placing product in oven and calcining at approximately 400 C;

placing the catalyst in a fixed bead multiple reactor;

in a heating vessel, combining a mixture of the feedstock oil and crude glycerin wherein the glycerin is approximately 1.2% times the amount of the weight of FFA in the feedstock oil;

heating the combined mixture to approximately at least 385 F for driving off moisture, said moisture to become less than about 0.25% of the resultant mixture;

pumping the resultant mixture across the catalyst bed in the fixed bead multiple reactor thereby producing an FFA reduced oil; and processing the FFA reduced oil through a centrifuge or other device to remove excess glycerin.

6. The method of claim 5 wherein the resultant mixture is pumped across the catalyst bed additional times as required for contact time for producing the FFA reduced oil.

7. A method for reducing the free fatty acid (FFA) of a feedstock oil containing approximately 2% to 100% FFA, the method comprising providing a heterogeneous calcined catalyst comprising approximately 1% to 95% colloidal silica, approximately 1% to 25% zinc oxide powder and approximately 0% to 5% copper oxide;

placing the catalyst in a fixed bead multiple reactor;

in a heating vessel, combining a mixture of the feedstock oil and crude glycerin wherein the glycerin is approximately 1.2% times the amount of the weight of FFA in the feedstock oil and wherein the FFA is approximately 0.1% to 75% by weight;

heating the combined mixture to approximately at least 385 F for driving off moisture, said moisture to become less than about 0.25% of the resultant mixture;

pumping the resultant mixture across the catalyst bed in the fixed bead multiple reactor thereby producing an FFA reduced oil; and removing excess glycerin from the FFA reduced oil.

* * * * *